(12) United States Patent
Singh et al.

(10) Patent No.: US 10,466,179 B2
(45) Date of Patent: Nov. 5, 2019

(54) SEMICONDUCTOR DEVICE INSPECTION OF METALLIC DISCONTINUITIES

(71) Applicant: Rudolph Technologies, Inc., Wilmington, MA (US)

(72) Inventors: Gurvinder Singh, Corcoran, MN (US); Wu Y. Han, Plano, TX (US); John Thornell, McKinney, TX (US); Chetan Suresh, Bloomington, MN (US); Wayne Fitzgerald, Andover, MA (US)

(73) Assignee: Rudoplh Technologies, Inc., Wilmington, MA (US)

( * ) Notice: Subject to any disclaimer, the term of this patent is extended or adjusted under 35 U.S.C. 154(b) by 0 days.

(21) Appl. No.: 15/933,362

(22) Filed: Mar. 22, 2018

(65) Prior Publication Data
US 2018/0275063 A1    Sep. 27, 2018

Related U.S. Application Data

(60) Provisional application No. 62/474,970, filed on Mar. 22, 2017.

(51) Int. Cl.
| | |
|---|---|
| *G01N 21/64* | (2006.01) |
| *H01L 21/67* | (2006.01) |
| *G01N 21/95* | (2006.01) |
| *G01N 21/88* | (2006.01) |
| *H01L 21/66* | (2006.01) |
| *G01N 21/84* | (2006.01) |
| *G01B 11/06* | (2006.01) |

(52) U.S. Cl.
CPC ..... *G01N 21/6489* (2013.01); *G01B 11/0608* (2013.01); *G01N 21/6456* (2013.01); *G01N 21/8422* (2013.01); *G01N 21/8806* (2013.01); *G01N 21/8851* (2013.01); *G01N 21/9501* (2013.01); *H01L 21/67288* (2013.01); *H01L 22/12* (2013.01); *G01B 2210/56* (2013.01); *G01N 21/9505* (2013.01); *G01N 2021/646* (2013.01); *G01N 2021/8461* (2013.01); *G01N 2021/8822* (2013.01); *G01N 2021/8883* (2013.01)

(58) Field of Classification Search
None
See application file for complete search history.

(56) References Cited

U.S. PATENT DOCUMENTS

| | | | | |
|---|---|---|---|---|
| 4,681,442 | A * | 7/1987 | Wagner | G01N 21/8806 250/559.44 |
| 5,208,648 | A * | 5/1993 | Batchelder | G01N 21/9505 356/237.1 |
| 2012/0126141 | A1* | 5/2012 | Pulisciano | G01B 11/25 250/459.1 |
| 2015/0192529 | A1* | 7/2015 | Sato | G01N 21/88 438/16 |

* cited by examiner

*Primary Examiner* — Edwin C Gunberg
(74) *Attorney, Agent, or Firm* — Todd R. Fronek; Larkin Hoffman Daly & Lindgren, Ltd.

(57) ABSTRACT

Concepts presented herein relate to approaches for performing substrate inspection. In one aspect, the concepts relate to detecting anomalies or candidate defects on the substrate based on contrast in images obtained of the substrate.

12 Claims, 3 Drawing Sheets

SEMICONDUCTOR DEVICE INSPECTION OF METALLIC DISCONTINUITIES

BACKGROUND

Current inspection of electronic devices such as wafers, circuit boards, flat panel displays, multichip modules and high-density packages use several different inspection techniques. These inspection techniques can be used during various times in the manufacturing process in order to identify various conditions associated with manufacturing of the devices.

SUMMARY

Concepts presented herein relate to approaches for performing substrate inspection. In one aspect, the concepts relate to detecting anomalies or candidate defects on the substrate based on contrast in images obtained of the substrate.

DETAILED DESCRIPTION

Figure 1:
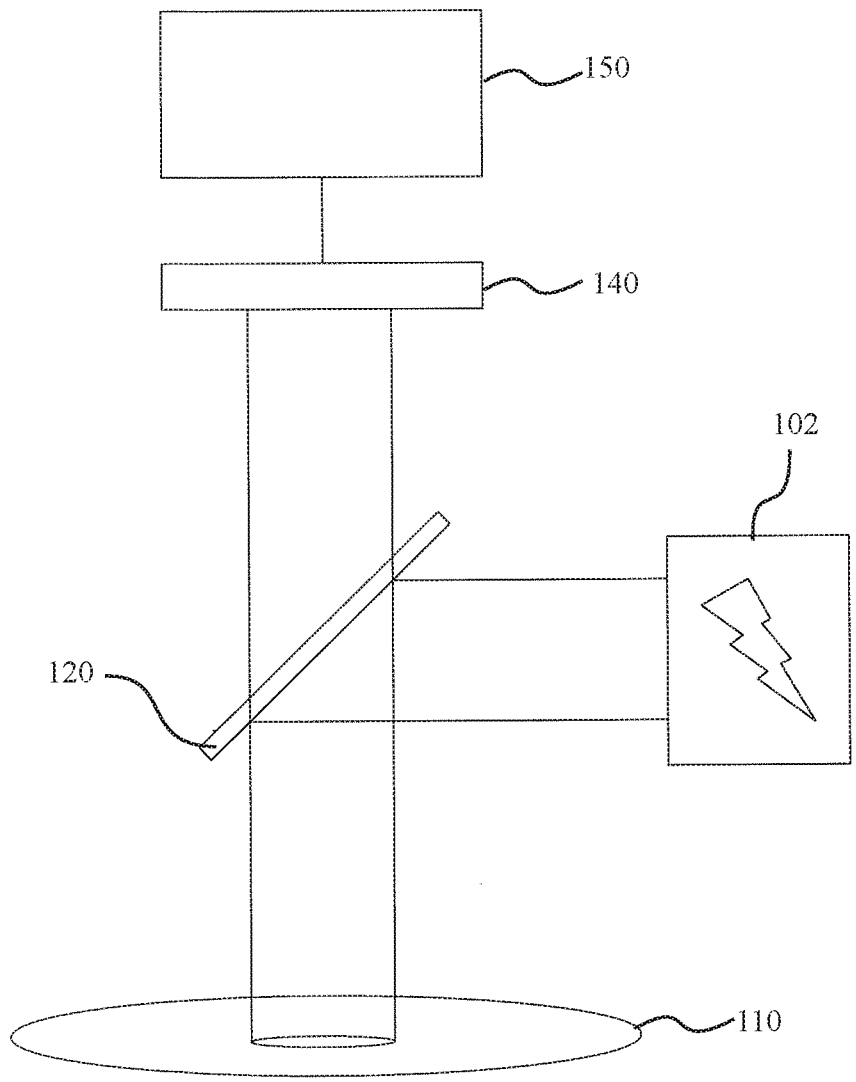
FIG. 1 is a schematic diagram of an example optical system.

As schematically illustrated in FIG. 1, an optical system 100 includes a light source 102 provided to illuminate a substrate 110. As used herein, the term 'light' is intended to encompass all forms of electromagnetic radiation at any useful wavelength or wavelengths. An excitation light (e.g., ultraviolet) from the light source 102 is transmitted to a filter and beam splitter 120 which passes and reflects different wavelengths of light. The beam splitter 120 reflects the excitation light from the source 102 onto the substrate 110. Portions of the substrate 110, for example, non-fluorescent metal leads and non-metallic layers, reflect light impinging thereon. Light reflected from these portions of the substrate 110 maintains the same wavelength as the excitation light from the source 102. In some embodiments, the excitation light from the source 102 is in the ultraviolet range of wavelengths. Since the beam splitter 120 reflects the excitation light from the source 102, light returned from the source at the incident wavelength is reflected from the beam splitter 120 and away from a sensor 140.

Some of the excitation light from source 102 is incident on materials, e.g. organic materials, which fluoresce upon absorbing light at an excitation wavelength. This phenomenon is well known to those skilled in the art. Generally, the wavelength of the fluorescent light emitted from the substrate is of a longer wavelength than the excitation light, however this is not always the case. The system 100 then, must separate excitation light from the source 102 from the fluorescent light emitted from the substrate so that the fluorescent light may be incident upon a sensor 140. This is done by filtering light returned from the substrate using a wavelength sensitive filter or more preferably, by using a wavelength specific beam splitter 140. In a preferred embodiment the beam splitter is dichroic, reflecting light at one range of wavelengths and passing light at another range of wavelengths. This type of beam splitter can be set up as a long pass filter, short pass filter, or a band pass filter. Of particular interest are beam splitters that will pass fluorescent light, but reflect excitation light.

Optical system 100 can include several different optical components as desired to capture images of substrate 110. These components are not illustrated for clarity and brevity reasons, but may include lenses, collimators, beam splitters, filters, etc. for focusing, collection and collimation of light. Additionally, optical system 100 can include different light sources (which may not be shown) and sensors configured to capture various types of images as desired. Light source 102 may emit light in a single wavelength or a narrow band of wavelengths (e.g. monochromatic) or across a wider band of wavelengths that is exclusive of the wavelengths of fluorescent light that is of interest. Source 102 may include an incandescent or fluorescent bulb or may constitute one or more light emitting diodes (LEDs). Lasers may also be used. While the example shown in the figures is of a simple brightfield imaging arrangement, alternative optical techniques darkfield and interferometry are also contemplated.

In accordance with one example embodiment of optical system 100, excitation light is absorbed by material on the substrate, the material fluorescing as a result. In this example embodiment, the light emitted by the foreign material has a wavelength which is longer than the excitation source light, which is in this embodiment in the ultraviolet range. For example, the emitted light may be in the visible light spectrum. The fluorescent light that is emitted from the substrate in the direction of the beam splitter 120 is transmitted through the beam splitter 120, which in this instance acts as a long pass filter.

Light which is transmitted through the beam splitter 120 is directed to the sensor 140, through other optical components such as lenses, filters, etc. In one embodiment, the sensor 140 is a time delay integration (TDI) camera, area scan camera, hyperspectral camera or other sensor type (e.g., one that captures color information) as desired. These sensors may be of a charge coupled device (CCD) or complementary metal-oxider semiconductor (CMOS) arrangement, as desired. The sensor 140 is coupled to a controller 150. The controller 150, in one embodiment, includes a computer, I/O facilities to couple the sensor 140 to the computer, a processor, memory, and optionally network capabilities that allow the controller 150 to be connected to other local or remote controllers or to a computer network over which instructions are received and data is sent. The controller 150, in one embodiment, controls imaging and image processing related to operation of the optical system 100.

Controller 150 may also control mechanisms (e.g., a stage and/or a robot), to coordinate automated handling and processing of substrates. The controller 150 can work in local mode, handling all operations on the local system or can distribute some of its functions to remote controllers. An equipment front end module (EFEM) or other handler (not shown) can be coupled to a separate controller that coordinates the provision and removal of substrates from a stage. The stage can be controlled by a motion controller that may be separate from, but which works in conjunction with, controller 150.

Example functions performed by the controller 150 include obtaining raw image data from the optical system 100 (e.g., from sensor 140) and producing data relevant for image analysis. Various different analytical processes utilized by controller 150 include, for example, identifying anomalies, forming overlay images, classifying defects, analyzing thresholds, calculating thickness of various substrates, analyzing wafer yield and analyzing capture selection for images of the substrate. Given these analyses, various actions can be implemented, including performing further substrate processing steps, modifying substrate production processes, discarding substrates, approving substrates and/or approving a portion of substrates.

Alternatively, or in addition thereto, metallic materials on the substrate do not fluoresce and typically produce a grayscale value of zero or near zero when exposed to ultraviolet light. If a layer of non-metallic material is positioned on top of the metallic layer, the resulting grayscale value will be greater than zero.

In one example, optical system 100 can be useful in identifying candidate defects, i.e. anomalies. For example, the candidate defects can indicate potential electrical failure on a surface of a substrate. In one embodiment, once a candidate defect is identified by optical system 100, a second optical processing technique can be used, such as dark field illumination or interferometry in order to provide further information as to whether the candidate defect is likely to cause failure of a device, can be removed and/or is merely a nuisance defect and can be ignored.

Figure 2:
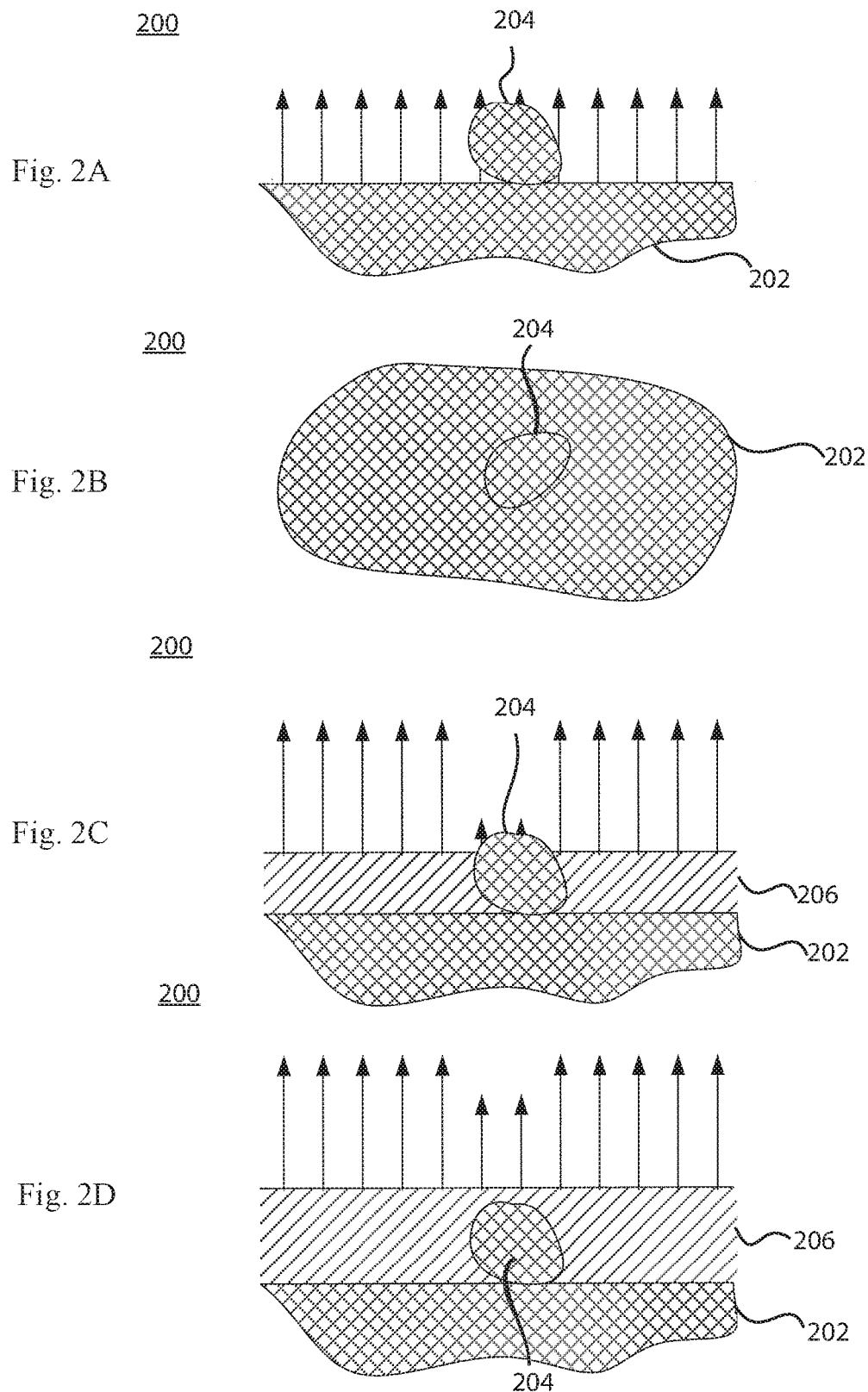
FIG. 2A is a schematic illustration of a candidate defect positioned on a metallic layer.
FIG. 2B is a schematic illustration of a top view of a candidate defect positioned on a metallic layer.
FIG. 2C is a schematic illustration of a candidate defect positioned on a metallic layer and protruding from a non-metallic layer.
FIG. 2D is a schematic illustration of a candidate defect positioned on a metallic layer and covered by a non-metallic layer.

FIG. 2A illustrates an example area of interest (AOI) 200 of a substrate having a metallic layer 202 having a candidate defect 204 (herein illustrated as a metallic nodule) positioned thereon. In one embodiment, the metallic layer 202 is an electrical lead of a semiconductor device. In this example, the candidate defect 204 is a metallic nodule defined with a particular height H extending above a top surface of the metallic layer 202. While this example related to the height H, other embodiments can relate to a size or other characteristics of the nodule. Typical imaging techniques such as visible wavelength brightfield imaging often have difficulty in distinguishing between the metallic layer 202 and the candidate defect 204. There is little contrast in intensity of light reflected from a top of metallic layer 202 and a top of candidate defect 204. For example, FIG. 2A schematically illustrates arrows indicative of intensity reflected from metallic layer 202 and candidate defect 204. Moreover, FIG. 2B schematically illustrates a top image of the candidate defect 204 and surrounding metallic layer 202, wherein limited contrast exists between the candidate defect 204 and surrounding metallic layer 202. Fluorescence imaging systems have difficulty with candidate defects 204 such as those illustrated in FIGS. 2A and 2B as the metal from which these objects are formed does not fluoresce. Accordingly, the sensor 140 will record very dark images that have a very low contrast; this makes it very difficult to discern the presence of a candidate defect 204.

Depending on the height H of the candidate defect 204, the defect may cause an electrical failure or other issue that will create a device failure if not removed. However, in other situations, the height H of the candidate defect 124 can be such that it is unlikely to cause an electrical failure. As schematically illustrated in FIG. 2C, the candidate defect 204 protrudes from a non-metallic (e.g., a dielectric or passivation coating) layer 206. A fluorescent image of the AOI 200 illustrated in FIG. 2C will produce an image with varying intensity. In particular, fluorescent light emitted by layer 206 will have a larger intensity (schematically shown by longer arrows in FIG. 2C) than light returned from the candidate defect 204 (schematically shown by shorter arrows in FIG. 2C) as the arrangement of the optical system 100 filters out any light that might be returned from the non-fluorescent metallic candidate defect 204. An image captured by the sensor 140 shows a bright layer 206 surrounding a dark candidate defect 204 with sufficient contrast between the layer and the candidate defect to reliably resolve the candidate defect 204.

FIG. 2D schematically illustrates another scenario where non-metallic, fluorescent layer 206 is of a height to completely cover the candidate defect 204. In this scenario, images of a top of the AOI 200 will still vary in intensity. As schematically illustrated in FIG. 2D, light emitted from layer 206 because of fluorescence will have a larger intensity where there is no candidate defect present and have a smaller intensity where candidate defect 204 is present.

Figure 3:
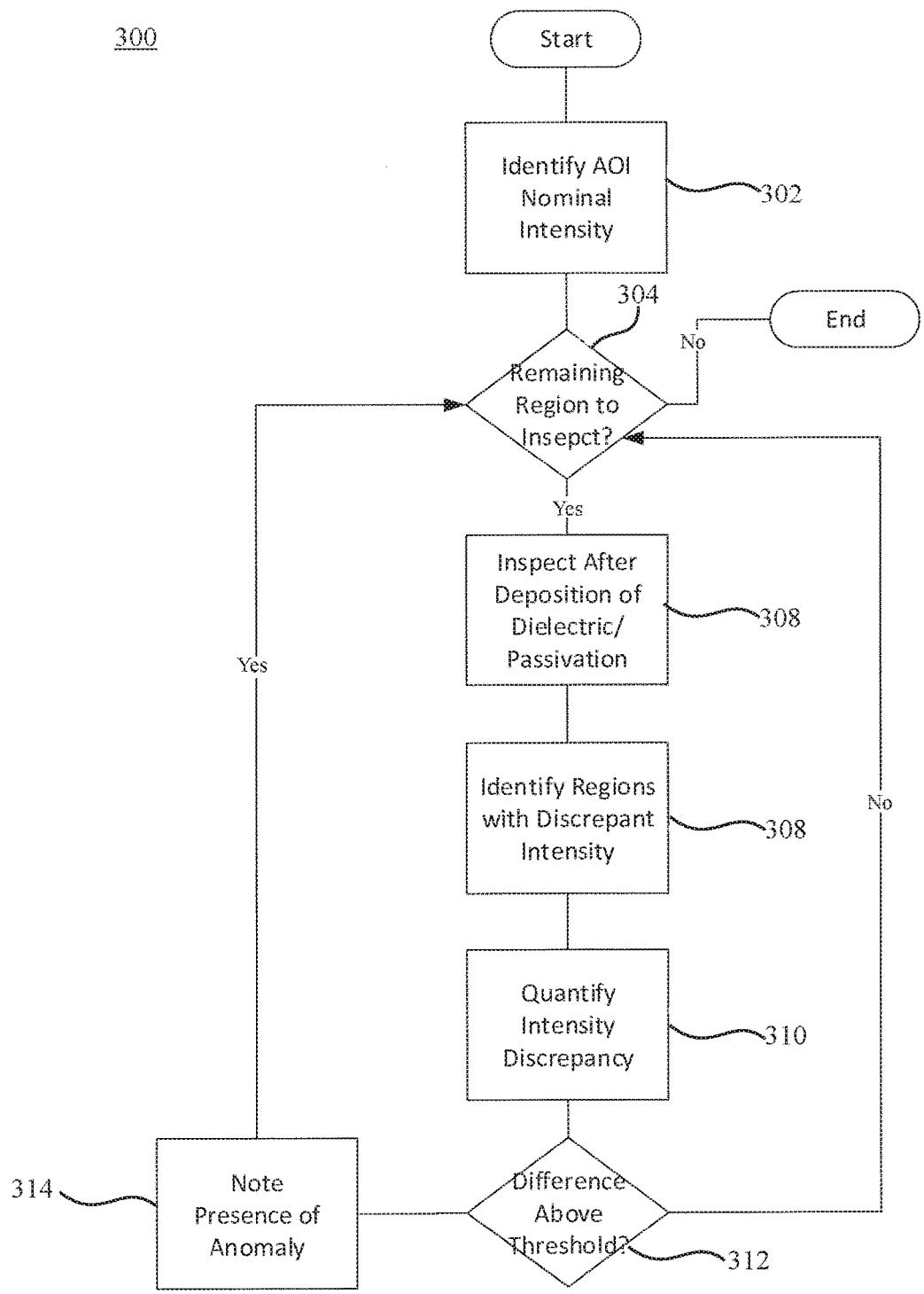
FIG. 3 is a flow diagram of a method for inspecting a substrate.

FIG. 3 is an example flow diagram of a method 300 for inspecting a substrate as discussed above. Step 302 includes identifying an area of interest nominal intensity. The nominal intensity can be identified, for example using a model based on a fluorescent material characteristic or based on multiple images of similar areas of interest. As discussed above, metallic areas will have a lower nominal intensity, while fluorescent, non-metallic areas will have a higher nominal intensity. Given the nominal intensity identification, inspection for regions of the substrate can be identified and a determination is made as to whether regions for inspection remain at step 304. After deposition of a non-metallic dielectric or passivation layer, a particular region is inspected at step 306. The inspection takes place using optical system 100 as discussed above.

Given the inspection conducted at step 306, regions with discrepant intensity are identified at step 308. This identification can be conducted by comparing the information received during the inspection at 306 and the nominal intensity identified at step 302. Given the comparison, the intensity discrepancy can be quantified in several different ways. In one example, a number of pixels that differ in the particular region between the inspection image and model can be selected as the quantification of the discrepancy. In other examples, the quantification can be selected as a difference in grayscale value for pixels in the particular region. Regardless of the particular quantification, a difference value can be compared to a particular threshold at step 312. If the difference is below the threshold, no anomaly or candidate defects are detected and method 300 returns to step 304. If the difference is above the threshold, method 300 proceeds to step 314, where a presence of an anomaly or candidate defect is noted. Method 300 then proceeds to step 304. If further regions remain to be inspected, method 300 repeats steps 306-312 for additional regions. If there are no regions left to be inspected, method 300 ends.

Based on the presence of one or more anomalies on a substrate, further processing techniques can be employed. For example, additional optical techniques can be used on various regions that include anomalies so as to provide a likelihood that a candidate defect will cause an electrical failure. In one example, a region can be inspected using dark field illumination based on a position of the candidate defect. Using dark field illumination, the height of the candidate defect can be calculated. In one example, a particular threshold can be selected such that if the height of the candidate defect is greater than a selected threshold, it will be more likely that the resulting semiconductor device will fail, whereas if the height is below the threshold, the candidate defect will be unlikely to cause an electrical fail.

Given the extent of the height calculation, further processing techniques can then be determined, such as cleaning the semiconductor device, approving the semiconductor device for further processing, discarding the semiconductor device and others.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A method of inspecting a substrate, comprising:
    capturing an image of the substrate using fluorescent light emitted from the substrate, the substrate identified by a nominal intensity;
    analyzing the image to identify a top surface of a metallic layer of the substrate, a fluorescent, non-metallic layer of the substrate and candidate defects indicative of a metallic nodule extending from the top surface and positioned with respect to the non-metallic layer of the substrate, wherein analyzing includes calculating intensity values for areas of interest in the image and comparing the intensity values to the nominal intensity;
    calculating a height of the metallic nodule based on identification of the candidate defects; and
    determining whether the non-metallic layer covers the metallic nodule or protrudes from the non-metallic layer.

2. The method of claim 1, wherein analyzing includes calculating an intensity associated with the candidate defects and an intensity associated with the non-metallic layer.

3. The method of claim 2, further comprising determining a difference between the intensity associated with the candidate defects and the intensity associated with the non-metallic layer.

4. The method of claim 1, wherein calculating a height of the metallic nodule includes using darkfield illumination.

5. The method of claim 1, wherein calculating a height of the metallic nodule includes using an interferometer.

6. The method of claim 1, wherein the height is calculated as a distance from the top surface of a metallic layer positioned below the non-metallic layer to a top of the metallic nodule.

7. A semiconductor device manufactured by the method of claim 1.

8. A method of inspecting a substrate, the substrate used in forming a semiconductor device, comprising:
    capturing a first image of the substrate using fluorescent light emitted from the substrate, the substrate including a first metallic layer covered by a fluorescent, non-metallic layer;
    identifying a non-uniform region of the substrate from the captured image, the non-uniform region indicating candidate defects, each candidate defect indicative of a metallic discontinuity associated with the substrate;
    directing darkfield illumination to the non-uniform region based on a location of one or more of the candidate defects;
    capturing a second image in a response to reflection of the darkfield illumination at the non-uniform region; and
    analyzing the second image in order to determine a likelihood of the candidate defect causing electrical failure of the semiconductor device due to a second metallic layer positioned on the non-metallic layer being electrically connected to the first metallic layer through the metallic discontinuity.

9. The method of claim 8, wherein the likelihood of the candidate defect causing electrical failure is based on a height of the candidate defect.

10. The method of claim 8, wherein identifying a non-uniform region of the substrate includes analyzing intensity values in the first image.

11. The method of claim 8, further comprising scrapping the substrate if the likelihood of the candidate defect causing electrical failure is above a threshold.

12. A semiconductor device manufactured by the method of claim 8.

* * * * *